May 25, 1965 O. O. DUNHAM Plant Pat. 2,519
CHRYSANTHEMUM PLANT
Filed March 4, 1964
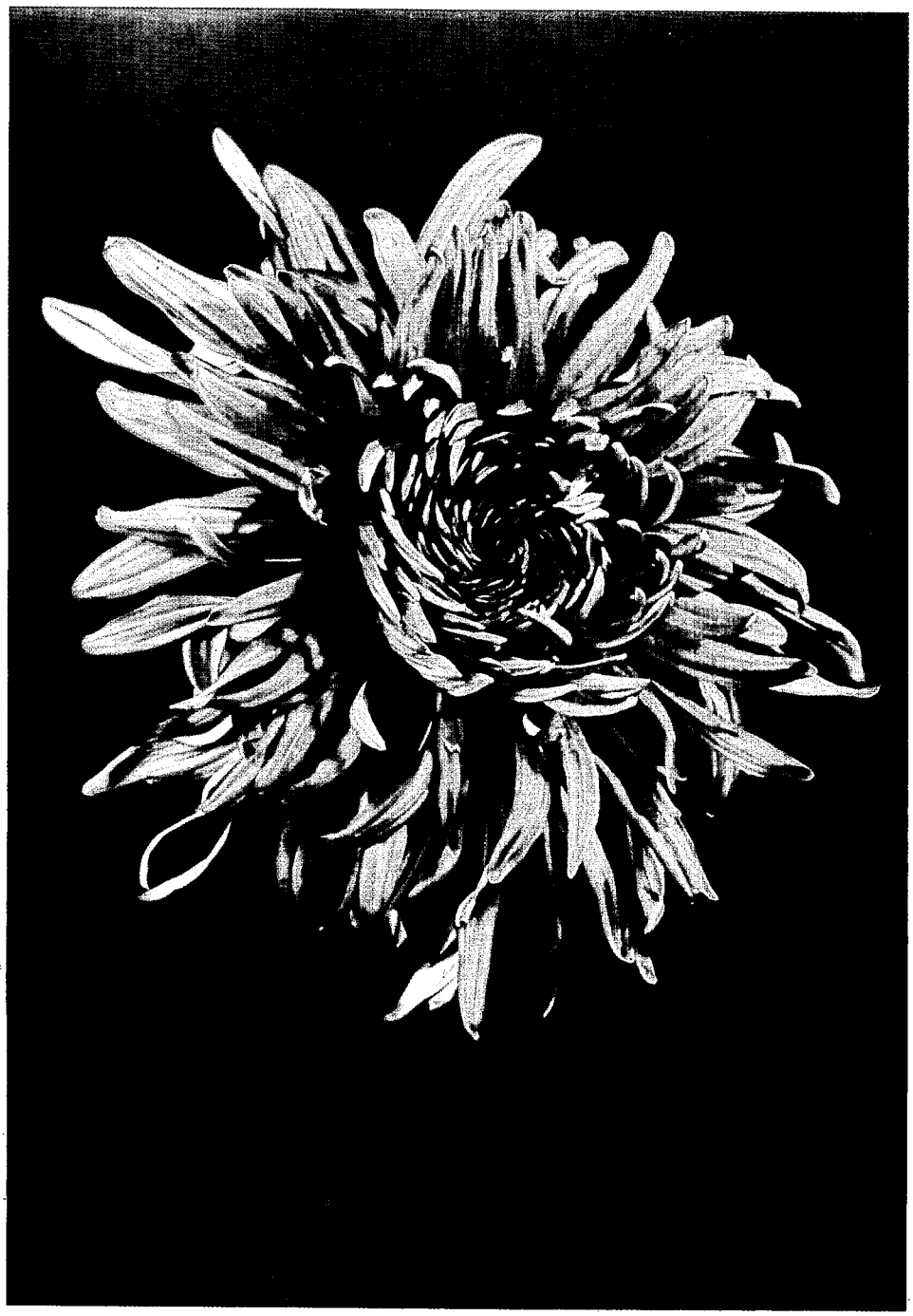
Inventor
O. O. Dunham
by Robb & Robb
attorneys United States Patent Office Plant Pat. 2,519
Patented May 25, 1965

2,519
CHRYSANTHEMUM PLANT

Orville O. Dunham, Niles, Mich., assignor to Stern's Nurseries, Inc., Geneva, N.Y., a corporation of New York Filed Mar. 4, 1964, Ser. No. 349,516
1 Claim. (Cl. Plt.—82)

My present invention relates to a new and distinct variety of chrysanthemum plant produced as a result of crossing the variety "Peaceful," an unpatented variety of my own origination, with the variety "Picturesque," another variety of my own origination and likewise unpatented.

The instant variety, which is one of many developed by me during the course of extensive and careful crossing of a large number of varieties, has resulted in the new variety which enjoys many of the characteristics of the parents, although readily distinguishable therefrom, both varieties being what I term exhibition garden chrysanthemums.

I have purposely selected the variety "Peaceful" as the seed parent so as to furnish a reflexing cactus-like bloom, with the pollen parent "Picturesque" providing the incurving central portion of the bloom and vigorous plant habit.

All the foregoing is a part of this intensive program of development which I have undertaken over many years to provide new and distinct varieties with better characteristics in the garden chrysanthemum field.

The result of the hybridization previously referred to has been to produce my present new and distinct variety of chrysanthemum plant characterized by the generally Strong Purplish-Red color of its blooms with petals having much lighter reverses of Pale Purplish-Pink, reflexing outer petals and tightly incurving central petals on strong sturdy stems in a plant having upright habit and weather resistant blooms.

More specifically, the blooms of my new variety are of the Strong Purplish-Red general tonality with petal reverses of much lighter Pale Purplish-Pink (Nickerson Color Fan published by the Munsell Color Company), the decided contrast between the outer reflexing petals and the tightly incurving central petals providing a novel appearance not heretofore present in these or similar varieties. As grown in the vicinity of Niles, Michigan in uniform culture, plants of my new variety are distinctly weather resistant and of medium height.

As will be understood from the foregoing, my new variety derives a number of characteristics from both parents, but what I consider better characteristics than either separately and my new variety differs from both parents and other known varieties in the several respects heretofore enumerated.

Under the conditions of culture previously mentioned, which have been undertaken in the region of Niles, Michigan, plants of my new variety grow vigorously with a decided contrast in petal colors and a quantity of blooms by early October.

My new variety when grown in the region of Niles, Michigan, blooms from early October until a killing frost with profuse numbers of blooms on each plant.

My new variety has been asexually reproduced by cuttings in the vicinity of Niles, Michigan, observations made herein as a basis, being during mid-October.

My new variety has been found to retain its distinctive characteristics through successive asexual reproduction.

The accompanying drawing forming a part hereof shows a typical bloom of my new variety of chrysanthemum in a color illustration which I believe is reasonably accurate and particularly as to color illustrations of its character is at least representative.

The following is a detailed description of my new variety of chrysanthemum plant, the color references being to the Nickerson Color Fan published by the Munsell Color Company:

*Description*

Parentage: Seedling.
*Seed parent.*—"Peaceful" (unpatented).
*Pollen parent.*—"Picturesque" (unpatented).
Classification: Botanic—*Chrysanthemum indicum.*

*Flower*

Blooming habit: Blooms profusely and continuously from early October until a killing frost.
Bud:
*Size.*—Large.
*Form.*—Short with flat top.
Not affected by hot or wet weather.
Color:
*When sepals first divide.*—7.5RP 8/5 Light Purplish-Pink.
*When petals begin to unfurl.*—7.5RP 6½ Deep Purplish-Pink.
*When half blown.—Inside of petals*—5RP 5/10 Moderate Purplish-Red. Reverse of petals—2.5RP 9/2 Pale Purplish-Pink.
*Sepals.*—Of no consequence.
*Calyx.*—Shape—funnel. Size—large and broad. Aspect—hairy.
*Peduncle.*—Length — medium. Aspect — rough. Strength—stiff and erect. Bud opens well.
Bloom:
*Size.*—Very large. Average size when fully expanded—5½ to 6 inches.
*Borne.*—In clusters.
*Stems.*—Long and strong.
*Form.*—When first open—flat. Permanence—retains its form to the end.
*Petalage.*—Very double. Innumerable petals under normal conditions.
Color:
*Center of flower.*—7.5RP 3/9 Deep Purplish-Red with lighter reverses.
*Outer petals.*—7.5RP 4/11 Strong Purplish-Red.
*Base of petals.*—5RP 3/9 Deep Purplish-Red.
*Inside of petals.*—7.5RP 4/11 Strong Purplish-Red.
*Reverse of petals.*—7.5RP 9/2 Pale Purplish-Pink.
*General tonality from a distance.*—7.5RP 5/12 Strong Purplish-Red with lighter petal reverses.
*Discoloration.*—General tonality at end of: First week—7.5RP 4/11 Strong Purplish-Red with lighter reverses. Second week—retains same color. Third week—retains same color.
Petals:
*Texture.*—Thick and soft. Not affected by hot or wet weather.
*Appearance.*—Inside—Velvety. Outside—satiny.
*Form.*—Pointed.
*Arrangement.*—Irregular.
*Persistence.*—Hang on and dry.
*Lastingness.*—On the plant—very long. As cut flower—very long.
Genital organs:
*Stamens, anthers.*—Medium.
*Arrangement.*—Regular around styles.
*Stamens, filaments.*—Medium.
*Styles.*—Columnar.
*Ovaries.*—All enclosed in calyx.
Plant:
*Form.*—Bush.
*Growth.*—Vigorous, upright and branching.
Foliage:
*Size.*—Very large.
*Quantity.*—Abundant.
*Shape.*—Lanceolate.

*Texture.*—Upper side — velvety. Under side—Smooth. Ordinary ribs and veins.

*Edge.*—Serrated.

I claim:

A new and distinct variety of chrysanthemum plant substantially as herein disclosed, characterized as to novelty by the generally Strong Purplish-Red color of its blooms with the petals having much lighter reverses of Pale Purplish-Pink, the reflexing outer petals and tightly incurving central petals, strong, sturdy stems, upright habit and large weather resistant blooms.

No refernces cited.

ABRAHAM G. STONE, *Primary Examiner.*